(12) United States Patent
Slocum (10) Patent No.: US 12,251,148 B2
(45) Date of Patent: Mar. 18, 2025

(54) TRI-ROLL THREAD ELECTRIC SURGICAL IMPACT TOOL

(71) Applicant: Zimmer, Inc., Warsaw, IN (US)

(72) Inventor: Alexander Slocum, Bow, NH (US)

(73) Assignee: Zimmer, Inc., Warsaw, IN (US)

(*) Notice: Subject to any disclaimer, the term of this patent is extended or adjusted under 35 U.S.C. 154(b) by 556 days.

(21) Appl. No.: 17/589,456

(22) Filed: Jan. 31, 2022

(65) Prior Publication Data

US 2022/0240998 A1    Aug. 4, 2022

Related U.S. Application Data

(60) Provisional application No. 63/144,285, filed on Feb. 1, 2021.

(51) Int. Cl.
*A61B 17/92* (2006.01)
*B25D 11/10* (2006.01)
*A61B 17/00* (2006.01)

(52) U.S. Cl.
CPC .......... *A61B 17/92* (2013.01); *B25D 11/102* (2013.01); *B25D 11/104* (2013.01);
(Continued)

(58) Field of Classification Search
CPC ..... A61B 17/92; A61B 17/925; B25D 11/102; B25D 11/104; B25D 11/106
See application file for complete search history.

(56) References Cited

U.S. PATENT DOCUMENTS

| 974,267 A | 11/1910 | Hennessy et al. |
| 2,270,929 A * | 1/1942 | Bugg ............... B25D 11/102 74/56 |

(Continued)

FOREIGN PATENT DOCUMENTS

| AU | 2019203142 A1 | 11/2019 |
| AU | 2020200771 A1 | 2/2020 |

(Continued)

OTHER PUBLICATIONS

"International Application Serial No. PCT/US2021/058776, International Search Report mailed Feb. 9, 2022", 5 pgs.

(Continued)

*Primary Examiner* — Nicholas W Woodall
(74) *Attorney, Agent, or Firm* — SCHWEGMAN LUNDBERG & WOESSNER, P.A.

(57) ABSTRACT

Disclosed herein are surgical impact tools and methods of use thereof. The surgical impact tools can include a roller assembly, an impact structure, and a tool holder. The roller assembly can be connected to a motor and include a plurality of rollers supported by a respective roller arm. The impact structure can define a spring and an impact cavity including forward and reverse impact surfaces. The impact structure can include a wall comprising a plurality of thread elements connected to the wall and engageable with the roller assembly. Each of the thread elements can include a pair of helical end surfaces and a pair of axially extending surfaces that are engaged by the plurality of rollers. During use rotation of the roller assembly against the helical ends of the thread elements can cause axial movement of the impact structure to apply a load on the spring and generate impact forces.

20 Claims, 6 Drawing Sheets

(52) U.S. Cl.
CPC .. *B25D 11/106* (2013.01); *A61B 2017/00203* (2013.01); *A61B 2017/00398* (2013.01); *A61B 2017/00734* (2013.01); *A61B 2017/925* (2013.01); *A61B 2017/928* (2013.01)

(56) References Cited

U.S. PATENT DOCUMENTS

| | | | |
|---|---|---|---|
| 2,323,375 A * | 7/1943 | Bugg | B25D 11/102 74/56 |
| 2,353,321 A * | 7/1944 | Snodgrass | B25D 11/102 175/212 |
| 2,542,695 A | 2/1951 | Neff et al. | |
| 2,576,851 A | 11/1951 | Newman | |
| 2,655,921 A | 10/1953 | Haboush | |
| 2,657,383 A * | 11/1953 | Ford | B25D 11/102 173/203 |
| 3,450,215 A | 6/1969 | Emery | |
| 3,472,323 A | 10/1969 | Hall | |
| 3,626,935 A | 12/1971 | Pollock et al. | |
| 3,752,161 A | 8/1973 | Bent | |
| 4,298,074 A | 11/1981 | Mattchen | |
| 4,466,429 A | 8/1984 | Loscher et al. | |
| 4,651,833 A | 3/1987 | Karpf et al. | |
| 4,834,092 A | 5/1989 | Alexson et al. | |
| 5,057,112 A | 10/1991 | Sherman et al. | |
| 5,108,400 A | 4/1992 | Appel et al. | |
| 5,152,352 A | 10/1992 | Mandanis | |
| 5,163,519 A | 11/1992 | Mead et al. | |
| 5,210,918 A | 5/1993 | Wozniak et al. | |
| 5,282,805 A | 2/1994 | Richelsoph et al. | |
| 5,352,230 A | 10/1994 | Hood | |
| 5,353,230 A | 10/1994 | Maejima et al. | |
| 5,363,726 A | 11/1994 | Smith | |
| 5,431,660 A | 7/1995 | Burke | |
| 5,485,887 A | 1/1996 | Mandanis | |
| 5,553,675 A | 9/1996 | Pitzen et al. | |
| 6,126,694 A | 10/2000 | Gray, Jr. | |
| 6,159,214 A | 12/2000 | Michelson | |
| 6,264,660 B1 | 7/2001 | Schmidt et al. | |
| 6,264,661 B1 | 7/2001 | Jerger et al. | |
| 6,368,324 B1 | 4/2002 | Dinger | |
| 6,520,266 B2 | 2/2003 | Bongers-Ambrosius et al. | |
| 6,626,913 B1 | 9/2003 | Mckinnon et al. | |
| 6,814,738 B2 | 11/2004 | Naughton et al. | |
| 6,868,918 B2 | 3/2005 | Shinohara | |
| 7,090,677 B2 | 8/2006 | Fallin et al. | |
| 7,189,241 B2 | 3/2007 | Yoon et al. | |
| 7,637,327 B2 | 12/2009 | Grunig | |
| 8,002,776 B2 | 8/2011 | Liu et al. | |
| 8,393,409 B2 | 3/2013 | Pedicini | |
| 8,444,647 B2 | 5/2013 | Walen et al. | |
| 8,465,492 B2 | 6/2013 | Estes | |
| 8,556,901 B2 | 10/2013 | Anthony et al. | |
| 8,602,124 B2 | 12/2013 | Pedicini | |
| 8,695,726 B2 | 4/2014 | Pedicini | |
| 8,894,654 B2 | 11/2014 | Anderson | |
| 8,936,105 B2 | 1/2015 | Pedicini | |
| 8,936,106 B2 | 1/2015 | Pedicini | |
| 9,168,154 B2 | 10/2015 | Behzadi | |
| 9,186,158 B2 | 11/2015 | Anthony et al. | |
| 9,198,675 B2 | 12/2015 | Nelson et al. | |
| 9,220,612 B2 | 12/2015 | Behzadi | |
| 9,554,965 B2 | 1/2017 | Foehrenbach | |
| 9,629,641 B2 | 4/2017 | Ferro et al. | |
| 9,649,202 B2 | 5/2017 | Behzadi et al. | |
| 9,877,734 B2 | 1/2018 | Anderson | |
| 9,901,354 B2 | 2/2018 | Pedicini | |
| 9,931,151 B2 | 4/2018 | Donald et al. | |
| 9,943,318 B2 | 4/2018 | Anthony et al. | |
| RE46,954 E | 7/2018 | Pedicini | |
| 10,028,754 B2 | 7/2018 | Johnson et al. | |
| RE46,979 E | 8/2018 | Pedicini | |
| 10,159,500 B2 | 12/2018 | Chavarria et al. | |
| 10,172,722 B2 | 1/2019 | Behzadi | |
| 10,245,160 B2 | 4/2019 | Behzadi | |
| 10,245,162 B2 | 4/2019 | Behzadi | |
| 10,251,663 B2 | 4/2019 | Behzadi | |
| 10,299,930 B2 | 5/2019 | Behzadi | |
| 10,342,591 B2 | 7/2019 | Pedicini | |
| 10,368,882 B2 | 8/2019 | Ferro et al. | |
| 10,413,425 B2 | 9/2019 | Behzadi | |
| 10,426,540 B2 | 10/2019 | Behzadi | |
| 10,441,244 B2 | 10/2019 | Behzadi | |
| 10,456,271 B2 | 10/2019 | Behzadi | |
| 10,463,505 B2 | 11/2019 | Behzadi | |
| 10,470,897 B2 | 11/2019 | Behzadi | |
| 10,478,318 B2 | 11/2019 | Behzadi et al. | |
| 10,568,643 B2 | 2/2020 | Johnson et al. | |
| 10,603,173 B2 | 3/2020 | Carr et al. | |
| RE47,963 E | 4/2020 | Pedicini | |
| 10,610,379 B2 | 4/2020 | Behzadi | |
| RE47,997 E | 5/2020 | Pedicini | |
| 10,653,533 B2 | 5/2020 | Behzadi | |
| 10,660,767 B2 | 5/2020 | Behzadi | |
| 10,729,559 B2 | 8/2020 | Behzadi et al. | |
| RE48,184 E | 9/2020 | Pedicini | |
| RE48,251 E | 10/2020 | Pedicini | |
| 11,013,503 B2 | 5/2021 | Pedicini | |
| 11,490,943 B2 | 11/2022 | Haiat et al. | |
| 11,918,268 B2 | 3/2024 | Doyle | |
| 11,925,359 B2 | 3/2024 | Slocum et al. | |
| 12,004,793 B2 | 6/2024 | Levy | |
| 12,064,158 B2 | 8/2024 | Marinkovich | |
| 12,070,256 B2 | 8/2024 | Slocum et al. | |
| 2004/0026097 A1 * | 2/2004 | Hecht | B25D 11/005 173/114 |
| 2007/0282345 A1 | 12/2007 | Yedlicka et al. | |
| 2010/0137760 A1 | 6/2010 | Schulz et al. | |
| 2011/0255927 A1 | 10/2011 | Boudreau et al. | |
| 2011/0270256 A1 | 11/2011 | Johnson et al. | |
| 2012/0172939 A1 | 7/2012 | Pedicini | |
| 2012/0215267 A1 | 8/2012 | Pedicini | |
| 2012/0259339 A1 | 10/2012 | Hood et al. | |
| 2013/0161050 A1 | 6/2013 | Pedicini | |
| 2013/0261681 A1 | 10/2013 | Bittenson | |
| 2014/0318819 A1 | 10/2014 | Pedicini | |
| 2014/0318823 A1 | 10/2014 | Pedicini | |
| 2015/0196343 A1 | 7/2015 | Donald et al. | |
| 2016/0199199 A1 | 7/2016 | Pedicini | |
| 2017/0020536 A1 | 1/2017 | Johnson et al. | |
| 2017/0056205 A1 | 3/2017 | Biegun et al. | |
| 2018/0001447 A1 * | 1/2018 | Lam | B25B 23/147 |
| 2018/0055518 A1 | 3/2018 | Pedicini | |
| 2018/0055552 A1 | 3/2018 | Pedicini | |
| 2018/0303496 A1 | 10/2018 | Johnson et al. | |
| 2018/0318089 A1 | 11/2018 | Carr et al. | |
| 2018/0338751 A1 * | 11/2018 | Pedicini | A61F 2/4603 |
| 2018/0360464 A1 | 12/2018 | Irvine | |
| 2019/0070719 A1 * | 3/2019 | Liang | B25D 11/104 |
| 2019/0167434 A1 | 6/2019 | Satterthwaite et al. | |
| 2019/0183554 A1 | 6/2019 | Pedicini | |
| 2019/0216521 A1 | 7/2019 | Chhatrala | |
| 2019/0247057 A1 | 8/2019 | Anderson | |
| 2019/0282286 A1 | 9/2019 | Pedicini | |
| 2022/0142693 A1 | 5/2022 | Slocum et al. | |
| 2022/0226033 A1 | 7/2022 | Slocum et al. | |
| 2022/0240946 A1 | 8/2022 | Slocum et al. | |
| 2022/0240947 A1 | 8/2022 | Marinkovich | |
| 2022/0273317 A1 | 9/2022 | Levy | |
| 2022/0323134 A1 * | 10/2022 | Lyon | A61B 17/92 |
| 2022/0361934 A1 | 11/2022 | Pedicini | |
| 2023/0240735 A1 | 8/2023 | Doyle | |
| 2024/0024012 A1 | 1/2024 | Dittrich et al. | |
| 2024/0299072 A1 | 9/2024 | Grimm et al. | |

FOREIGN PATENT DOCUMENTS

| | | |
|---|---|---|
| AU | 2021239844 A1 | 10/2022 |
| AU | 2017320580 B2 | 4/2023 |
| AU | 2021378282 A1 | 6/2023 |
| AU | 2022227599 A1 | 8/2023 |
| AU | 2021378282 | 10/2024 |
| CA | 3063569 A1 | 11/2018 |
| CA | 3209081 A1 | 8/2022 |

(56) References Cited

FOREIGN PATENT DOCUMENTS

| | | |
|---|---|---|
| CA | 3211071 A1 | 9/2022 |
| CH | 701397 A2 | 1/2011 |
| CN | 2423872 Y | 3/2001 |
| CN | 204863450 U | 12/2015 |
| CN | 109070324 A | 12/2018 |
| CN | 108602180 B | 12/2022 |
| CN | 116801840 A | 9/2023 |
| CN | 117414174 A | 1/2024 |
| DE | 102010017726 A1 | 1/2011 |
| EP | 0290375 A1 | 11/1988 |
| FR | 2054809 A5 | 5/1971 |
| JP | H06229427 A | 8/1994 |
| JP | H06304193 | 11/1994 |
| JP | H10174689 A | 6/1998 |
| JP | 2002144255 A | 5/2002 |
| JP | 2005506211 A | 3/2005 |
| JP | 2010524577 A | 7/2010 |
| JP | 2012504987 A | 3/2012 |
| JP | 2013036488 A | 2/2013 |
| JP | 2015517341 A | 6/2015 |
| JP | 2016202560 A | 12/2016 |
| JP | 2017024167 | 2/2017 |
| JP | 2018502689 A | 2/2018 |
| JP | 2019524165 A | 9/2019 |
| JP | 2019177138 A | 10/2019 |
| JP | 2019198645 A | 11/2019 |
| JP | 2020521560 | 7/2020 |
| JP | 2020530332 A | 10/2020 |
| JP | 2020185421 A | 11/2020 |
| JP | 7127068 B2 | 8/2022 |
| JP | 2022166207 A | 11/2022 |
| JP | 7366968 B2 | 10/2023 |
| JP | 7375104 B2 | 10/2023 |
| JP | 7404463 B2 | 12/2023 |
| JP | 2023551117 A | 12/2023 |
| JP | 2024013234 A | 1/2024 |
| JP | 2024504977 A | 2/2024 |
| JP | 2024505231 A | 2/2024 |
| JP | 2024505239 A | 2/2024 |
| JP | 2024505543 A | 2/2024 |
| JP | 2024507954 A | 2/2024 |
| JP | 2024126020 A | 9/2024 |
| WO | WO-8802246 A2 | 4/1988 |
| WO | WO-8906516 A1 | 7/1989 |
| WO | WO-2008130904 A2 | 10/2008 |
| WO | WO-2016112397 A1 | 7/2016 |
| WO | 2018044348 | 3/2018 |
| WO | 2018217250 | 11/2018 |
| WO | WO-2022103835 A1 | 5/2022 |
| WO | WO-2022159704 A1 | 7/2022 |
| WO | WO-2022165215 A1 | 8/2022 |
| WO | WO-2022165223 A1 | 8/2022 |
| WO | WO-2022165357 A1 | 8/2022 |
| WO | WO-2022182772 A1 | 9/2022 |

OTHER PUBLICATIONS

"International Application Serial No. PCT/US2021/058776, Written Opinion mailed Feb. 9, 2022", 8 pgs.
"International Application Serial No. PCT/US2022/013312, International Search Report mailed Jun. 24, 2022", 6 pgs.
"International Application Serial No. PCT/US2022/013312, Invitation to Pay Additional Fees mailed May 3, 2022", 5 pgs.
"International Application Serial No. PCT/US2022/013312, Written Opinion mailed Jun. 24, 2022", 10 pgs.
"International Application Serial No. PCT/US2022/014368, International Search Report mailed May 30, 2022", 7 pgs.
"International Application Serial No. PCT/US2022/014368, Invitation to Pay Additional Fees mailed Apr. 5, 2022", 10 pgs.
"International Application Serial No. PCT/US2022/014368, Written Opinion mailed May 30, 2022", 8 pgs.
"International Application Serial No. PCT/US2022/014380, International Search Report mailed Jun. 24, 2022", 6 pgs.
"International Application Serial No. PCT/US2022/014380, Invitation to Pay Additional Fees mailed May 3, 2022", 5 pgs.
"International Application Serial No. PCT/US2022/014380, Written Opinion mailed Jun. 24, 2022", 7 pgs.
"International Application Serial No. PCT/US2022/017537, International Search Report mailed Jun. 1, 2022", 4 pgs.
"International Application Serial No. PCT/US2022/017537, Written Opinion mailed Jun. 1, 2022", 5 pgs.
Budimir, Miles, "What is a rack and roller pinion?", [Online]. Retrieved from the Internet: <https://www.motioncontroltips.com/rack-roller-pinion/>, (Nov. 10, 2017), 13 pgs.
Nexen, "Rack and Roller Pinion System", [Online]. Retrieved from the Internet: <https://www.nexengroup.com/nxn/products/prod-nav/lp/Roller+Pinion+System>, (Accessed online Apr. 27, 2021), 10 pgs.
"U.S. Appl. No. 17/587,794, Notice of Allowance mailed Nov. 15, 2023", 10 pgs.
"U.S. Appl. No. 17/587,866, Notice of Allowance mailed Apr. 11, 2024", 17 pgs.
"U.S. Appl. No. 17/678,807, Notice of Allowance mailed Feb. 14, 2024", 16 pgs.
"Australian Application Serial No. 2021378282, First Examination Report mailed Mar. 7, 2024", 3 pgs.
"European Application Serial No. 21820393.3, Response Filed Dec. 14, 2023 to Communication pursuant to Rules 161(1) and 162 EPC mailed Jul. 6, 2023", 10 pgs.
"European Application Serial No. 23186404.2, Extended European Search Report mailed Nov. 23, 2023", 8 pgs.
"U.S. Appl. No. 17/587,794, Response filed Aug. 28, 2023 to Restriction Requirement mailed Jun. 27, 2023", 7 pgs.
"U.S. Appl. No. 17/587,794, Restriction Requirement mailed Jun. 27, 2023", 7 pgs.
"International Application Serial No. PCT/US2021/058776, International Preliminary Report on Patentability mailed May 25, 2023", 10 pgs.
"International Application Serial No. PCT/US2022/013312, International Preliminary Report on Patentability mailed Aug. 3, 2023", 12 pgs.
"International Application Serial No. PCT/US2022/014368, International Preliminary Report on Patentability mailed Aug. 10, 2023", 10 pgs.
"International Application Serial No. PCT/US2022/014380, International Preliminary Report on Patentability mailed Aug. 10, 2023", 9 pgs.
"International Application Serial No. PCT/US2022/014596, International Preliminary Report on Patentability mailed Aug. 10, 2023", 7 pgs.
"International Application Serial No. PCT/US2022/017537, International Preliminary Report on Patentability mailed Sep. 7, 2023", 7 pgs.
U.S. Appl. No. 18/222,830, filed Jul. 17, 2023, Linear Electric Surgical Hammer Impact Tool.
"International Application Serial No. PCT US2022 014596, International Search Report mailed May 10, 2022", 4 pgs.
"International Application Serial No. PCT US2022 014596, Written Opinion mailed May 10, 2022", 5 pgs.
"U.S. Appl. No. 17/523,540, Notice of Allowance mailed Apr. 22, 2024", 10 pgs.
"Australian Application Serial No. 2021378282, Response filed May 22, 2024 to First Examination Report mailed Mar. 7, 2024", 8 pgs.
"Australian Application Serial No. 2022211325, First Examination Report mailed Apr. 29, 2024", 3 pgs.
"Australian Application Serial No. 2022211325, Response filed Jul. 19, 2024 to First Examination Report mailed Apr. 29, 2024", 17 pgs.
"Australian Application Serial No. 2022212126, First Examination Report mailed Apr. 26, 2024", 3 pgs.
"Australian Application Serial No. 2022212126, Response Filed Jul. 2, 2024 to First Examination Report mailed Apr. 26, 2024", 16 pgs.
"Australian Application Serial No. 2022212275, First Examination Report mailed May 15, 2024", 2 pgs.

(56) References Cited

OTHER PUBLICATIONS

"Australian Application Serial No. 2022212275, Response Filed Jun. 19, 2024 to First Examination Report mailed May 15, 2024", 14 pgs.
"Australian Application Serial No. 2022214931, First Examination Report mailed May 7, 2024", 3 pgs.
"Australian Application Serial No. 2022214931, Response filed Jul. 26, 2024 to First Examination Report mailed May 7, 2024", 9 pgs.
"Australian Application Serial No. 2022227599, First Examination Report mailed Apr. 18, 2024", 2 pgs.
"Australian Application Serial No. 2022227599, Response Filed Sep. 27, 2024 to First Examination Report mailed Apr. 18, 2024", 14 pgs.
"Australian Application Serial No. 2023206091, First Examination Report mailed Apr. 19, 2024", 4 pgs.
"Australian Application Serial No. 2023206091, Response filed Jul. 5, 2024 to First Examination Report mailed Apr. 19, 2024", 13 pgs.
"European Application Serial No. 22703776.9, Response Filed Mar. 11, 2024 to Communication pursuant to Rules 161(1) and 162 EPC mailed Aug. 30, 2023", 9 pgs.
"European Application Serial No. 22704684.4, Response filed Mar. 18, 2024 to Communication pursuant to Rules 161(1) and 162 EPC mailed Sep. 7, 2023", 17 pgs.
"European Application Serial No. 22705238.8, Response Filed Mar. 18, 2024 to Communication pursuant to Rules 161(1) and 162 EPC mailed Sep. 8, 2023", 172 pgs.
"European Application Serial No. 22705250.3, Response Filed Mar. 18, 2024 to Communication pursuant to Rules 161(1) and 162 EPC mailed Sep. 8, 2023", 15 pgs.
"European Application Serial No. 22713111.7, Response Filed Apr. 15, 2024 to Communication pursuant to Rules 161(1) and 162 EPC mailed Oct. 4, 2024", 8 pgs.
"European Application Serial No. 24161610.1, Extended European Search Report mailed Jul. 10, 2024", 6 pgs.
"Japanese Application Serial No. 2023-117628, Notification of Reasons for Refusal mailed May 28, 2024", w/ English translation, 7 pgs.
"Japanese Application Serial No. 2023-527766, Notification of Reasons for Refusal mailed Apr. 16, 2024", w/ English translation, 6 pgs.
"Japanese Application Serial No. 2023-544157, Notice of Reasons for Rejection mailed Apr. 23, 2024", w/ English translation, 5 pgs.
"Japanese Application Serial No. 2023-546065, Notification of Reasons for Refusal mailed Apr. 16, 2024", w/ English Translation, 15 pgs.
"Japanese Application Serial No. 2023-546135, Notification of Reasons for Refusal mailed Apr. 16, 2024", w/ English Translation, 9 pgs.
"Japanese Application Serial No. 2023-546333, Notification of Reasons for Refusal mailed Apr. 16, 2024", w/ English translation, 8 pgs.
"Japanese Application Serial No. 2023-552050, Notification of Reasons for Rejection mailed Jul. 2, 2024", W/English Translation, 5 pgs.
"U.S. Appl. No. 17/581,316, Response filed Oct. 14, 2024 to Restriction Requirement mailed Aug. 14, 2024", 7 pgs.
"U.S. Appl. No. 17/581,316, Restriction Requirement mailed Aug. 14, 2024", 5 pgs.
"Canadian Application Serial No. 3,200,838, Examiners Rule 86(2) Report mailed Aug. 21, 2024", 4 pgs.
"European Application Serial No. 23186404.2, Response Filed Jul. 23, 2024 to Extended European Search Report mailed Nov. 23, 2023", 16 pgs.
"Japanese Application Serial No. 2023-117628, Response Filed Aug. 23, 2024 to Notification of Reasons for Refusal mailed May 28, 2024", W/ English Claims, 11 pgs.
"Japanese Application Serial No. 2023-527766, Notification of Reasons for Refusal mailed Jul. 30, 2024", w/ English Translation, 8 pgs.
"Japanese Application Serial No. 2023-527766, Response filed Jul. 11, 2024 to Notification of Reasons for Refusal mailed Apr. 16, 2024", W/ English Claims, 13 pgs.
"Japanese Application Serial No. 2023-552050, Resoponse Filed Sep. 24, 2024 to Notification of Reasons for Rejection mailed Jul. 2, 2024", W/ English Claims, 11 pgs.
"Japanese Application Serial No. 2023-527766, Response filed Oct. 29, 2024 to Notification of Reasons for Refusal mailed Jul. 30, 2024", W English Claims, 13 pgs.
"Japanese Application Serial No. 2023-544157, Response Filed Jul. 19, 2024 to Notice of Reasons for Rejection mailed Apr. 23, 2024", W English Claims, 13 pgs.

* cited by examiner

TRI-ROLL THREAD ELECTRIC SURGICAL IMPACT TOOL

PRIORITY CLAIM

The present application claims priority to U.S. Provisional Application No. 63/144,285, entitled "Tri-Roll Thread Cordless Electric Power Impact Tool," filed on Feb. 1, 2021; the contents of which are hereby incorporated by reference in their entirety.

FIELD OF THE DISCLOSURE

The present disclosure relates generally to surgical instruments and use thereof. More specifically, the present disclosure relates to roll thread electric surgical impact tools and methods of use thereof.

BACKGROUND

Orthopedic surgeons commonly utilize tools for cutting or carving bone that require a hammer or mallet to transmit an impaction force to the tool. An example is a broach tool used to prepare the proximal end of a femur to receive the stem of a hip implant. Such broaches can be used with a hammer wielded by the physician or with a pneumatic "jackhammer" like tool. However, striking a broach tool with a hammer can be tiresome and can cause high stresses on the physician's own joints, such as the shoulder joint. Furthermore, pneumatic impact tools require connection to an air hose, which can be inconvenient and can potentially limit the physician's ability to orient the tool in the desired manner.

SUMMARY

The following, non-limiting examples, detail certain aspects of the present subject matter to solve the challenges and provide the benefits discussed herein, among others.

Example 1 is a surgical impact tool comprising: a motor; a roller assembly operatively connected to the motor and comprising a plurality of rollers, each of the plurality of rollers supported by a respective one of a plurality of roller arms; an impact structure defining a spring and an impact cavity including forward and reverse impact surfaces disposed on opposite ends of the impact cavity, the impact structure comprising a wall comprising a plurality of thread elements connected to the wall and engageable with the roller assembly, each of the thread elements including a pair of helical end surfaces and a pair of axially extending surfaces that are engaged by the plurality of rollers; a tool holder comprising an impact flange disposed within the impact cavity in between the forward and reverse impact surfaces; and wherein, during use: rotation of the roller assembly against the helical end surfaces of the thread elements causes axial movement of the impact structure to apply a load on the spring, and engagement of the roller assembly against the pair of axially extending surfaces of the thread elements allows the spring to be unloaded and cause the impact structure to engage the impact flange.

In Example 2, the subject matter of Example 1 optionally includes wherein in a forward impact mode the impact flange of the tool holder is movable toward a rear end of the impact cavity when a tool implement is pressed against a workpiece and in a rearward impact mode the impact flange of the tool holder is movable toward a forward end of the impact cavity when the impact tool is pulled away from the workpiece.

In Example 3, the subject matter of Example 2 optionally includes wherein the forward impact mode includes rotating the roller assembly in a first direction against first helical ends of the thread elements and the rearward impact mode includes rotating the roller assembly in a second direction opposite the first direction and against second helical ends of the thread elements.

In Example 4, the subject matter of any one or more of Examples 1-3 optionally include wherein the spring is formed integral with the wall.

In Example 5, the subject matter of any one or more of Examples 1-4 optionally include wherein the spring includes at least three coil springs.

In Example 6, the subject matter of any one or more of Examples 1-5 optionally include wherein the thread elements are connected to the wall by screws.

In Example 7, the subject matter of any one or more of Examples 1-6 optionally include a gearbox connected to the motor.

In Example 8, the subject matter of Example 7 optionally includes wherein the gearbox and the motor are disposed within the spring of the impact structure.

In Example 9, the subject matter of any one or more of Examples 1-8 optionally include a housing supporting the impact structure and the tool holder, the housing comprising a handle and a base; a trigger disposed in the handle; and a battery connected to the base.

In Example 10, the subject matter of Example 9 optionally includes a microphone disposed in the housing; and a controller operative to control operation of the impact tool by voice command.

Example 11 is a surgical impact tool comprising: a motor; a roller assembly operatively connected to the motor and comprising: a first roller supported by a first roller arm, a second roller supported by a second roller arm, and a third roller supported by a third roller arm; an impact structure defining a spring and comprising forward and reverse impact surfaces, the impact structure defining an impact cavity with the forward and reverse impact surfaces disposed on opposite ends of the impact cavity, the impact structure comprising a wall comprising first, second, and third thread elements connected to the wall and engageable with the roller assembly, each of the first, second, and third thread elements including a pair of helical end surfaces and a pair of axially extending surfaces that are engaged by the first, second, and third rollers, respectively; a tool holder comprising an impact flange disposed within the impact cavity in between the forward and reverse impact surfaces; and wherein, during use: rotation of the roller assembly against the helical end surfaces of the thread elements causes axial movement of the impact structure to apply a load on the spring, and engagement of the roller assembly against the pair axially extending surfaces of the thread elements allows the spring to be unloaded and cause the impact structure to engage the impact flange.

In Example 12, the subject matter of Example 11 optionally includes wherein in a forward impact mode the impact flange of the tool holder is movable toward a rear end of the impact cavity when a tool implement is pressed against a workpiece and in a rearward impact mode the impact flange of the tool holder is movable toward a forward end of the impact cavity when the impact tool is pulled away from the workpiece.

In Example 13, the subject matter of Example 12 optionally includes wherein the forward impact mode includes rotating the roller assembly in a first direction against first helical ends of the thread elements and the rearward impact mode includes rotating the roller assembly in a second direction opposite the first direction and against second helical ends of the thread elements.

In Example 14, the subject matter of any one or more of Examples 11-13 optionally include wherein the spring is formed integral with the wall.

In Example 15, the subject matter of any one or more of Examples 11-14 optionally include wherein the spring includes at least three coil springs.

In Example 16, the subject matter of any one or more of Examples 11-15 optionally include wherein the thread elements are connected to the wall by screws.

In Example 17, the subject matter of any one or more of Examples 11-16 optionally include a gearbox connected to the motor.

In Example 18, the subject matter of Example 17 optionally includes wherein the gearbox and the motor are disposed within the spring of the impact structure.

In Example 19, the subject matter of any one or more of Examples 11-18 optionally include a housing supporting the impact structure and the tool holder, the housing comprising a handle and a base; a trigger disposed in the handle; and a battery connected to the base.

In Example 20, the subject matter of Example 19 optionally includes a microphone disposed in the housing, and a controller operative to control operation of the impact tool by voice command.

In Example 21, the surgical impact tools, systems, and/or methods of any one or any combination of Examples 1-20 can optionally be configured such that all elements or options recited are available to use or select from.

BRIEF DESCRIPTION OF THE FIGURES

In the drawings, which are not necessarily drawn to scale, like numerals can describe similar components in different views. Like numerals having different letter suffixes can represent different instances of similar components. The drawings illustrate generally, by way of example, but not by way of limitation, various embodiments discussed in the present document.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

As an alternative to a pneumatic piston driven system, disclosed herein are electrically driven systems. Specifically, the electric surgical impact tools disclosed herein can include a motor operatively connected to a roller assembly operatively. The roller assembly can include a plurality of rollers and each of the plurality of rollers can be supported by a respective one of a plurality of roller arms. An impact structure can define a spring and an impact cavity that can include forward and reverse impact surfaces disposed on opposite ends of the impact cavity. The impact structure can include a wall comprising a plurality of thread elements connected to the wall and engageable with the roller assembly. Each of the thread elements can include a pair of helical end surfaces and a pair of axially extending surfaces that are engaged by the plurality of rollers. An impact flange of a tool holder element can be disposed within the impact cavity in between the forward and reverse impact surfaces.

During use, rotation of the roller assembly against the helical ends of the thread elements can cause axial movement of the impact structure to apply a load on the spring. Also, during use, engagement of the roller assembly against the axially extending surfaces of the thread elements can allow the spring to be unloaded and cause the impact structure to engage the impact flange.

As disclosed herein, in a forward impact mode the impact flange of the tool holder is moveable toward a rear end of the impact cavity when the tool implement is pressed against a workpiece (e.g., bone) and in a rearward impact mode the impact flange of the tool holder is movable toward a forward end of the impact cavity when the impact tool is pulled away from the workpiece. The forward impact mode can include rotating the roller assembly in a first direction against first helical ends of the thread elements and the rearward impact mode can include rotating the roller assembly in a second direction opposite the first direction and against second helical ends of the thread elements.

The surgical impact tools can include a housing supporting the impact structure and the tool holder. The housing can include a handle and a base. A trigger can be disposed in the handle and a battery can be connected to the base. A microphone and a controller can be disposed in the housing. The controller can be operative to control operation of the impact tool by voice command.

The above discussion is intended to provide an overview of subject matter of the present patent application. It is not intended to provide an exclusive or exhaustive explanation of the invention. The description below is included to provide further information about the present patent application.

Figure 1:
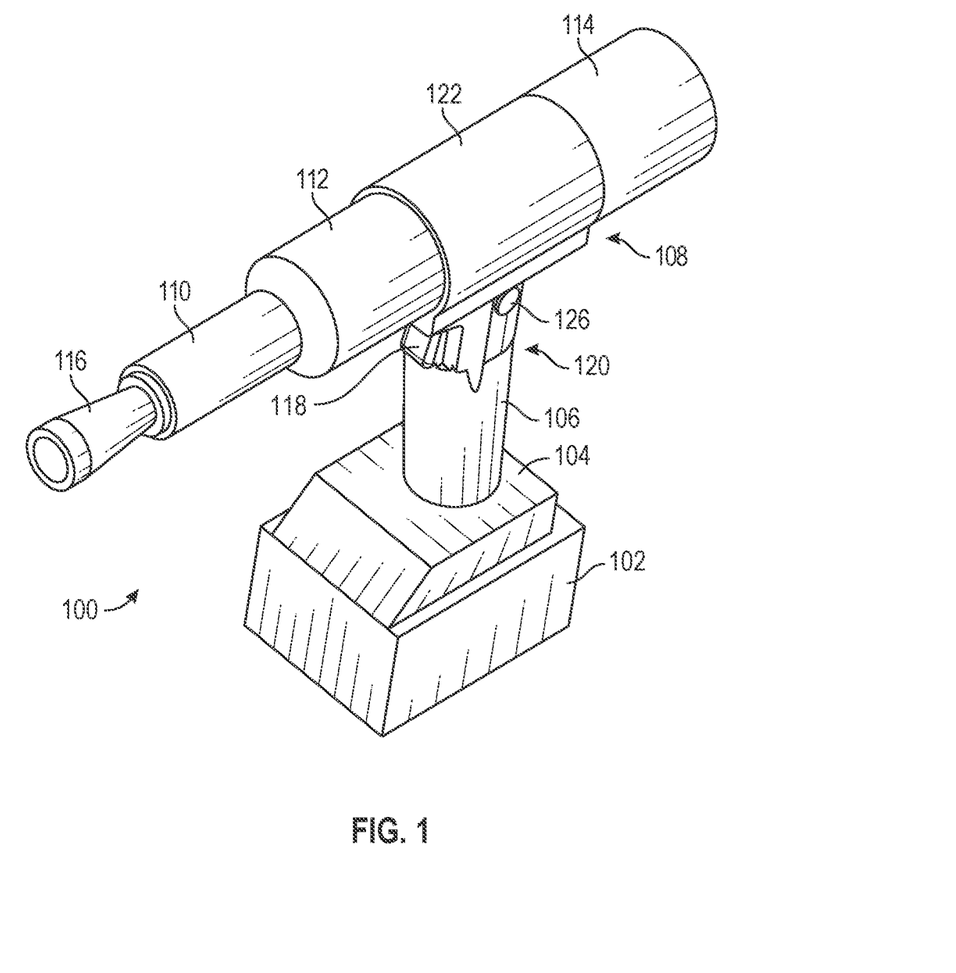
FIG. 1 shows a perspective view of a tri-roll thread electric surgical impact tool consistent with at least one example of this disclosure.

Turning now to the figures, FIG. 1 shows an example of a tri-roll thread electric surgical impact tool 100 consistent with at least one example of this disclosure. As disclosed herein, the tri-roll thread electric surgical impact tool 100, which can be cordless, can include a replaceable rechargeable battery pack 102 attached to a base 104, which can power and control electronics, such as controller 900 shown and describe below with respect to FIG. 9. A handle 106 can contain wires connected to a motor and/or sensors inside a main housing 108. A trigger 118 can provide manual on-off control and a speaker/microphone 126 can allow the user to speak instructions and hear suggestions from a system controller as disclosed herein. In other words, speaker/microphone 126 can allow the tri-roll thread electric surgical impact tool 100 to be controlled by voice commands. A handle system 120 can be attached to the main housing 108 by structure 122. The main housing 108 can include a distal portion 114, a middle portion 112, and a proximal portion 110. An orthopedic or other tool can be held in a tool holder 116.

Figure 2:
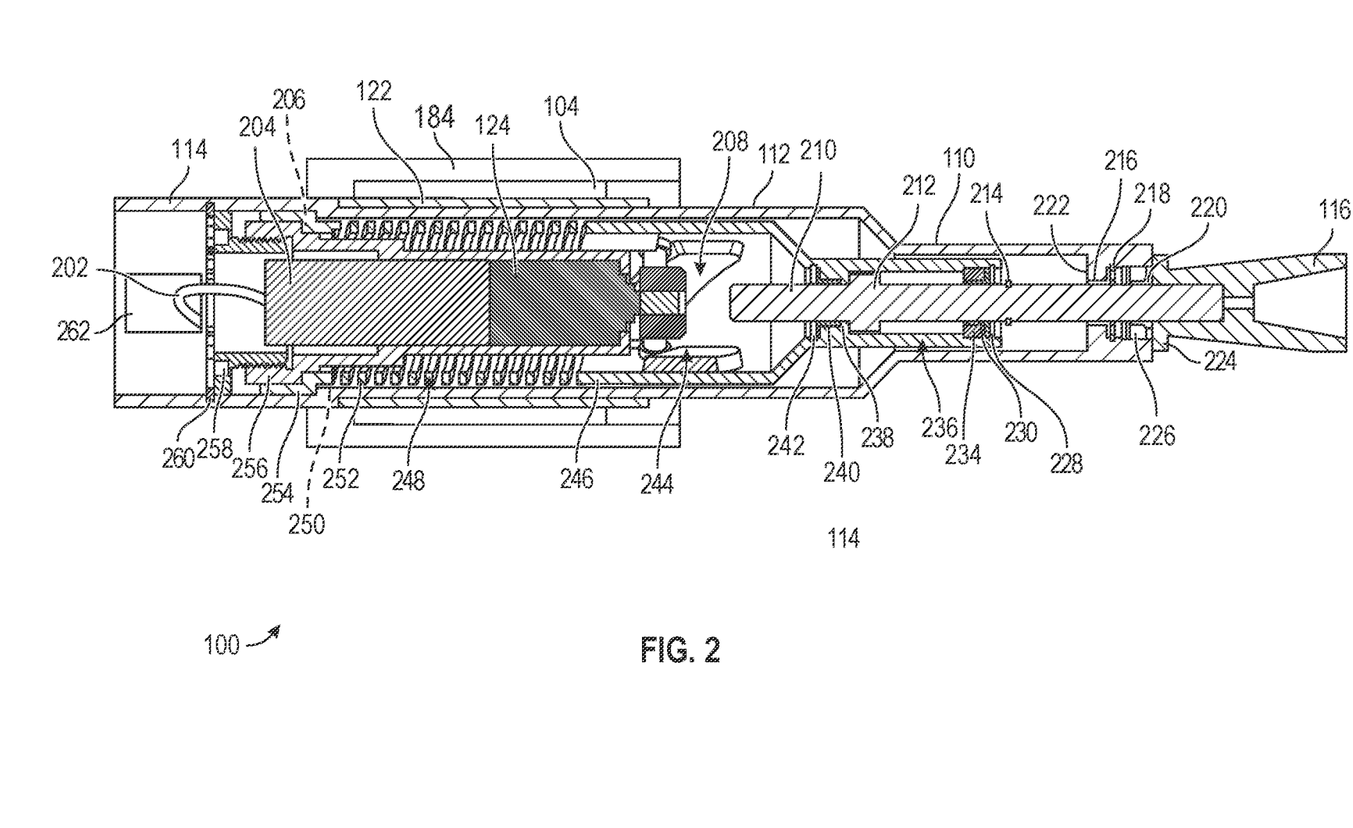
FIG. 2 shows a top cutaway view of a tri-roll thread electric surgical impact tool consistent with at least one example of this disclosure.

FIG. 2 shows a cross section from a top of the tri-roll thread electric surgical impact tool 100. The impact tool 100 can include a machined bi-directional (e.g., tension or compression) spring structure 248 with spring coils 252, shown in a neutral position in FIG. 2, and a tri-thread 244 actuated by a tri-roller 208 that can be attached directly to an output shaft of a gearbox 124. A motor 204 can be attached to the gearbox 124. For example, the gearbox 124 can be a ball-bearing-mini-motor-gearhead with a 62:1 ratio and can be used to provide 4 Joules of impact energy.

The motor 204 can have a power/position sensor data cable 202 that can extend out the back and down through a slot 262 in the distal outer housing section 114. An internal snap ring 260 can serve as a structure that a nut 258 can push against as it forces forward the motor housing structure 256. A step 206 on the motor housing structure 256 can push on a mating step 250 on the machined spring structure 254, which in turn can push on the step transition between the outer housing sections 114 and 112. The faces of these the steps 206 and 250 can all be machined perpendicular to a longitudinal axis such that radial misalignment between them at their proximal ends can be less than 0.1 mm. With an axial/diameter dimension ratio of about 5:1 this can produce a squareness requirement readily achievable for parts machined on a precision lathe.

To create a forward impact, a user can press the impact tool 100 forward so a distal face of flange 224 of tool holder 116 presses against a proximal face 226 of the structure 110. A forward portion 246 of the machined spring structure 248 can hold the tri-lobe thread elements (three) 244, which can be engaged by the tri-roller (three rollers) 208 that can be attached to the output shaft of the gearbox 124. When the shaft of the gearbox 124 rotates in one direction, the engagement of the rollers 208 with the threads 244 can cause the machined spring 248 to compress and draw backwards to store energy. A base 256 of the spring 248 can be fixed and not rotate due to a tight preload against the structure 108 by the nut 258.

As the spring 248 compresses, the proximal end 236 of the machined spring structure 248 can move distally. The proximal end 236 of the spring structure 248 can contain a snap ring 242 that can hold a flanged sliding contact bushing bearing 240 (e.g., a Rulon bearing) in place. The bushing bearing 240 can have an inner diameter of, for example, about 10 mm, which can slide over a shaft of a tool holder element 210. The proximal end of the tool holder element 210 can be guided by a flanged bushing bearing 216 that can be held in place by a snap ring 218. A sliding seal 220 can keep foreign matter out. When a striker flange 238 of the spring structure 248 reaches its fully distally retracted position, it can be then released by the tri-roller 208 reaching an end of travel and the turnaround portion of the tri-thread 244, to rapidly accelerate and cause proximal face of 238 to strike a distal face of the flange 212 on the tool holder element 210. Continued operation of the motor 204 of the impact tool 100 while the user is pushing forward on the impact tool 100 can repeat the process to drive a tool implement more and more into a work piece (e.g., broach cutting into a femur).

To enable assembly and to retract the tool, the machined spring structure 248 can have a collar 234 with bearing 230 and both are held in place by a snap ring 242. A snap ring 214 on the tool holder element 210 can move as the user pulls back on the impact tool 100 until it contacts a surface 222 and the flange 212 can approach the distal surface of collar 234. The motor 204 can then be operated in a reverse direction and the tri-roller 208 can engage the reversing thread surfaces of tri-thread 244 to extend the machined spring 252 to move the proximal structure 236 forward so collar 234 moves proximally away from collar 212. At the end of the thread engagement between tri-roller 208 and tri-threads 244, the spring 248 can snap back to deliver a retract blow between the distal face of collar 234 and the proximal face of flange 212. As the user continues pulling back on the impact tool 100 the motor rotation can repeat the process.

Figure 3:
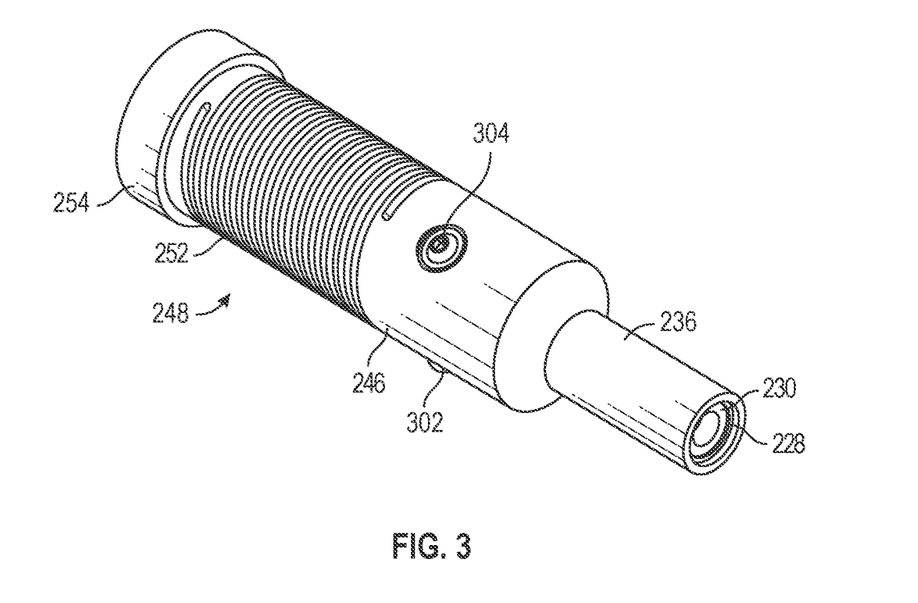
FIG. 3 shows a perspective view of a spring element subassembly of a tri-roll thread electric surgical impact tool consistent with at least one example of this disclosure.
Figure 4:
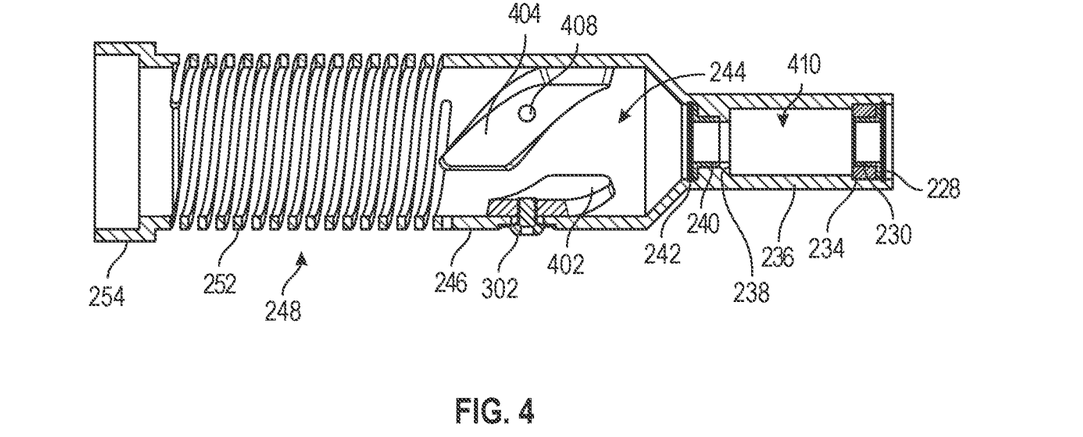
FIG. 4 shows a cutaway view of a spring element subassembly of a tri-roll thread electric surgical impact tool consistent with at least one example of this disclosure.

FIGS. 3 and 4 show the tri-spring threads/spring subassembly comprising the spring structure 248, the tri-threads 244, and bearings 240 and 230 held in place by snap rings 242 and 228, respectively. The impact cavity 77, sometimes called an impact chamber, can be bound on distal end by striker flange 238 and the proximal end by the collar 234, where the flange 212 of the tool holder element 210 can move back and forth in the impact cavity 77.

The spring coils 252 can be machined in the spring structure 248 so they are monolithic, and three coils 252 can be used to give the system greater lateral stability. The spring structure 248 can be made from a high strength stainless steel or a high strength steel such as a maraging steel (e.g., Aeromet 340). The tri-threads 244 can be made as inserts 506, 402, and 404 so that they can be precisely manufactured, hardened, and precision ground. The tri-threads 244 can then be attached by high strength flanged screws 302, 304, and 408, respectively. The tri-thread inserts oblong shape can mean that when held against the inside surface of the cylinder structure 246 they can resist twisting moments, but they can also be bonded in place in addition to being bolted by screws 302, 304, and—408 as insurance against loosening in the impact environment.

One manufacturing method that can be used to make the machined spring coils 252 integral with the spring structure 248 is to machine all but the spring coils 252 using machining operations, such as on a lathe. Then, an internal close fitting solid cylindrical mandrel can be inserted that is temporarily attached using a low melt alloy, such as those that have Gallium as a base metal. This can enable the spring coils 252 to be machined without risk of damage while machining.

Figure 5:
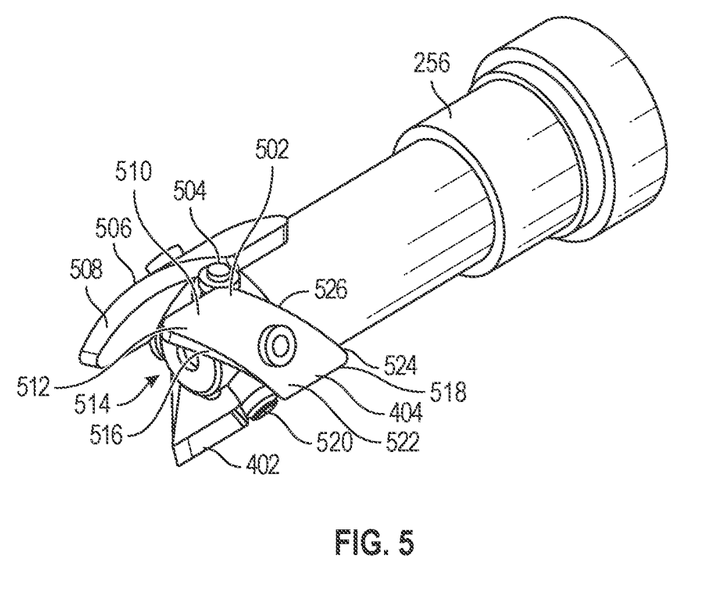
FIG. 5 shows a perspective view of core elements of a spring element subassembly of a tri-roll thread electric surgical impact tool consistent with at least one example of this disclosure.

FIG. 5 shows the tri-threads 244 without the spring structure 248 to which they are attached. Here the tri-roller 208 can be seen with its three thread rollers 504, 618, and 520 on central tri-arm structure 514 that can have a D-bore typically to enable transmission of high torque, although a keyed connection can be made to a gearmotor output shaft. The rollers 504, 618, and—520 can be ball bearings or for very high loads, needle roller bearings, and can be held in place by snap rings. Each tri-thread element, such as 404, can be sized to have a helical proximal forcing contact surface 502 and a helical distal forcing contact surface 522 for contact with a respective thread roller 520. For example, looking distally, as the motor gearbox 124 rotates the tri-roller 208 counterclockwise, a roller such as 520 can contact surface 516 compressing the springs 252 until the roller 520 gets to the radiused end 512. Axially straight surface 510 means that the spring can then thrust the proximal end 246 and 236 with impact chamber 410 in the proximal direction as the tri-roller continues to rotate counterclockwise can then come to contact helical thread surface 508 and the process can continue so multiple rapid strikes can be made. If the tri-roller 208 rotates clockwise, then corresponding opposite elements can be engaged, such as distal helical thread 526 to extend the springs 252 so when the roller 520 comes to the end of a thread and rolls around end 524 for example, the springs 252 can snap the proximal end 246 and 236 back in the distal direction for causing the collar 234 to impact the flange 212 of the tool holder element 210 for creating reverse impacts to aid in extraction of the tool implement.

The circumferential space between the helical thread surfaces and corresponding axially straight surfaces can be the diameter of a roller plus the distance travelled in the time it takes the spring to return while the motor keeps rotating. This can be only a few millimeters and can be determined based on the moving mass spring constant and spring compression.

Figure 6:
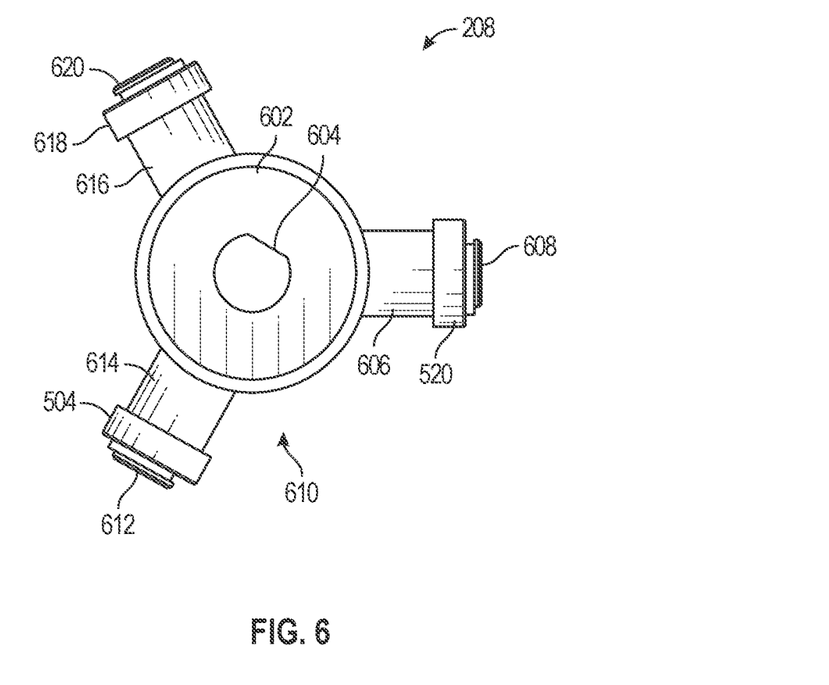
FIG. 6 shows an end plan view of a tri-roller subassembly consistent with at least one example of this disclosure.
Figure 7:
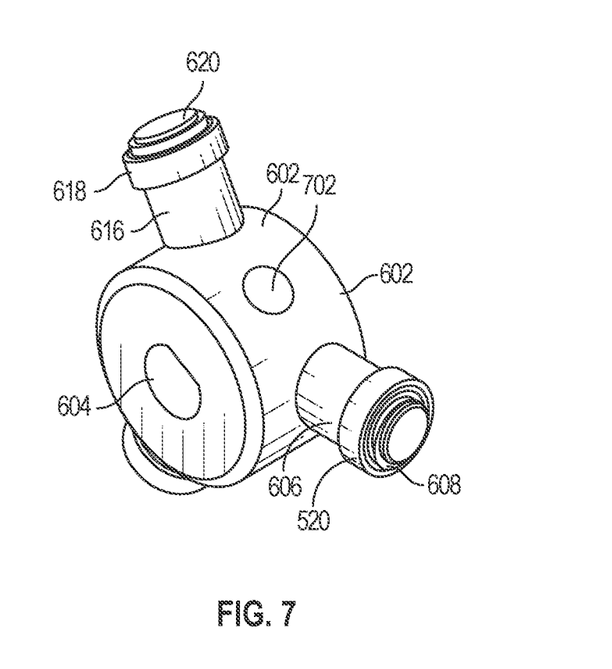
FIG. 7 shows a perspective view of a tri-roller subassembly consistent with at least one example of this disclosure.

FIGS. 5, 6, and 7 show the tri-roller subassembly 208 with its rollers 504, 618, and 520 on arms 614, 616, 606, which can protrude from central body 602 with D-shaped bore 604. Snap rings 612, 620, and 608 can hold their respective bearings in place. A set screw can be threaded into the threaded aperture 702 to axially secure the tri-roll subassembly 208 to the shaft of the motor gearbox 124 with a dimple on the shaft flat. The arms and body of the tri-roller subassembly 208 can be machined, or printed, or integrally molded to be integral (solid) for maximum strength when forming the tri-arm body 610.

Three arms and rollers 504, 618, and—520, and corresponding threads 506, 402, and—404, can provide radial stability while transmitting torque from the motor gearbox 124 without creating radial loads on the output shaft of the gearbox 124. In addition, the contact forces can be less than or equal to the torque from the gearbox 124 divided by the product of three and the radial distance from the roller center to the rotating shaft center. The rolling contact between the rollers 504, 618, and—520 and the thread elements 506, 402, and—404 can reduce contact stresses and wear, such as in the rounded end transition regions between the helical thread surfaces 508 and 516 and the axial return regions 510 and 518.

The roller assembly 208 include a hardened, ground tapered roller rotating in sealed, lifetime-lubricated ball bearings. Coupled with the use of dry lubricant surfaces in the thread grooves, this lifetime-lubrication can result in virtually maintenance-free operation. This is not a cam system which inherently has a varying gain (transmission ratio) as a function of position; rather this is a screw thread that has a constant transmission ratio, which means it responds in a linear manner, until it reverses.

The present disclosure herein combines the concept of a rollnut with the reversing screwdriver thread that instead of the threads crossing over themselves, the contact surfaces can be opposed and the motor can be reversed to reverse the direction. However, continuous motor rotation in either direction can result in continual oscillation with either a proximal or distal oscillation bias. Instead of a rotating threaded nut surrounding a screw shaft, the present disclosure uses a female thread that can be prevented from rotation but allowed to move axially, thus forming an internal threaded sleeve.

Engaging the threads can be an inside out tri-start rollnut where a tri-roller structure can be attached to the gearmotor output shaft. At the end of each arm of the tri-roller 208 can be a ball bearing with a convex (curved) profile outer race (either specially manufactured or a sleeve made and shrunk or bonded to the bearing outer ring). By using three rollers 504, 618, and—520 to engage the three internal threads 506, 402, and—404 of the coupler 248, the coupler 248 can be centered about the gearmotor axis of rotation and there can be no net radial loads on the gearbox shaft. The tri-roller 208 can experience axial loads and thus the gearmotor output shaft can have a snap ring groove to ensure the tri-roller 208 does not work its way off the shaft.

The tri-threads 506, 402, and—404 can be cut from one piece or individual inserts, which can be made in high volume using a powder metallurgy technique. The surfaces that the rollers 504, 618, and—520 can be contact finish ground after hardening. When cut with the center of an end mill tracing the helix, the contact surfaces will not be aligned with the longitudinal axis of the spiral. Furthermore, the outer rings of the bearing on the tri-roller arm ends 612, 620, and—608 are also not aligned perfectly with the longitudinal axis. Hence a slight taper of the surfaces (or end mill or grinding tool used to cut them) might be needed, such as, for example, a 1 degree taper. Furthermore, at the turn around zone at the end of travel, there can be a further mismatch potential between the roller and the thread turn around surface, which can be adjusted to ensure line contact. Note the differential radius can imply slipping and hence once again a crowned roller can be used.

The spring structure 248 can be machined from a tubular structure, and a triple start thread 252 can be used to help maximize lateral stability. A machined spring thread can be bi-directional and thus reloaded. Hence only one spring 248 can be needed for storing and releasing energy in either the forward or reverse motion for driving or extracting a tool respectively.

Figure 8:
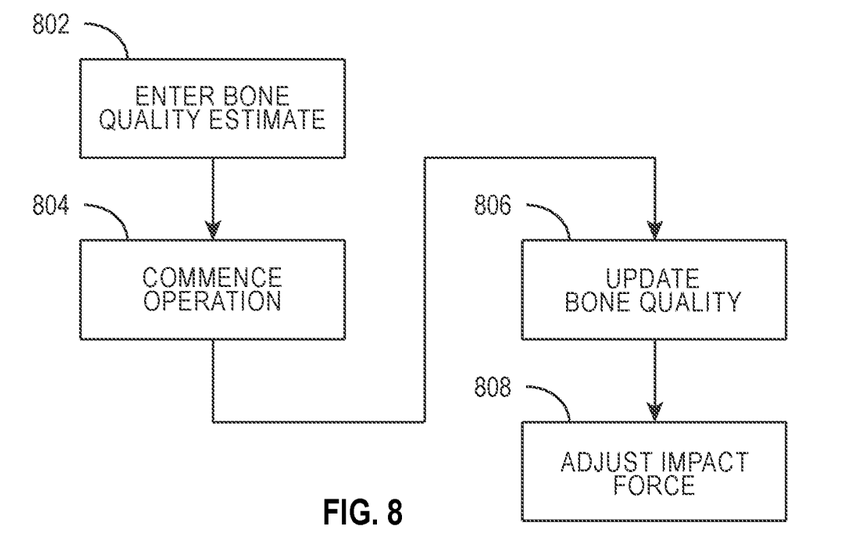
FIG. 8 shows a flowchart of logic usable for controlling a tri-roll thread electric surgical impact tool consistent with at least one example of this disclosure.

FIG. 8 shows a method for controlling a tri-roll thread electric surgical impact tool, such as impact tool 100, consistent with at least one example of this disclose. During and/or before a surgical procedure, a surgeon can enter an estimate of bone quality into a controller (802), the operation may commence (804). For example, bone quality scores can range from 1, poor quality bone, to 5 for high quality bone. Depending on the bone quality the tool may be set to deliver a predetermine impact force. For example, for low bone quality a low impact force can be set. For a higher bone quality, a higher impact force can be set.

During the operation, the bone quality can be updated (806), using a tool/position sensor sensing, based on how quick the tool is moving into the bone on the first few broaches. For example, if the broach is sliding in faster than expected due to weak cancellous bone (e.g., osteoporosis), the bone quality can be updated. The goal of the initial bone quality assessment can be to modulate the starting force (initial impact) and adjust the amount of subsequent impact modulation as the tool progresses into the bone (808). As the tool keeps impacting as broaches are increased in size, for example, the energy is monitored and remains unchanged when there is "maximum" broach movement down the femur canal (as measured by the position sensor) for example.

Updating the bone quality can be a continuous process. For example, as the position sensor notes that the broach or implant is not advancing forward as much ("medium movement forward"), which can indicate the end of travel. Continuing to impact the bone harder may damage the bone so the tool can automatically modulate the force down a specific percentage (e.g., a more significant decrease for weaker bone, less significant for stronger bone, etc.

Figure 9:
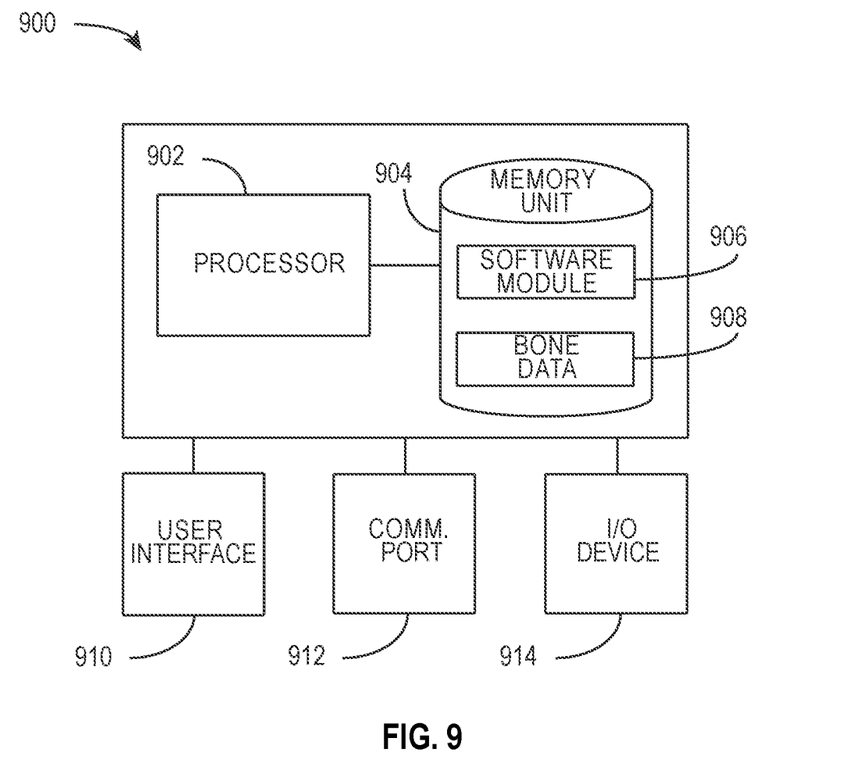
FIG. 9 shows a schematic of a controller consistent with at least one example of this disclosure.

FIG. 9 shows an example schematic of controller 900, in accordance with at least one example of this disclosure. As shown in FIG. 9, the controller 900 can include a processor 902 and a memory 904. The memory unit 904 can include a software module 906 and bone data 908. While executing on the processor 902, the software module 906 can perform processes receiving displacement data, determining bone quality, adjusting an impact force of a tool, etc., including, for example, one or more stages included in the method described herein.

As disclosed herein, the bone data 1208 can include formulas, lookup tables, actuarial tables, patient data, etc. that can be used to determine bone quality as disclosed herein. The bone data 1208 can also include data for correlating impact forces desirable for given bone qualities and for various sizing of tools, such as rasps and/or broaches. The controller 900 can also include a user interface 910, a communications port 912, and an input/output (I/O) device 914.

The user interface 910 can include any number of devices that allow a user to interface with the controller 900. Non-limiting examples of the user interface 910 can include a keypad, such as buttons located on a housing of a linear electric surgical hammer impact tool, a microphone, a display (touchscreen or otherwise and connected to controller via a wired or wireless connection), etc.

As an example, a surgeon, as he or she is observing the impact, can speak "less force," "more force," "faster," "slower," etc. and it will be understood that the impact tool 100 can be controlled by the user to meet their needs and style of use using his or her voice. The controller 900 can learn to respond to a particular user.

For the controller 900 to obtain less force it can control the distance of acceleration and current to a coil structure to vary the force and hence the acceleration of the impact element. The impact force can be proportional to energy, which is the product of one half the mass of the impact element and its velocity squared. "Faster" spoken by the user can mean that the controller 900 would cause the impact element to reciprocate back and forth faster. The controller 900 can operate in current control mode, to generate the desired force, and the voltage follows according to the speed as the impact element accelerates.

The communications port 912 may allow the controller 900 to communicate with various information sources and devices, such as, but not limited to, remote computing devices such as servers or other remote computers. For example, remote computing devices may maintain data, such as patient scan data, that can be retrieved by the controller 900 using the communications port 912. Non-limiting examples of the communications port 912 can include, Ethernet cards (wireless or wired), Bluetooth® transmitters and receivers, near-field communications modules, etc.

The I/O device 914 can allow the controller 900 to receive and output information. Non-limiting examples of the I/O device 914 can include, sensors, such as Hall effect sensors, a camera (still or video), a microphone, etc. For example, the I/O device 914 can allow the controller 900 to directly receive patient data from a CT scanning device, x-ray machine, etc. As another example, the I/O device 914 can include a Hall effect sensor that transmits one or more signals received by the processor 902. The processor 902 can then determine a position of the tri-roller element and/or an impact force to be generated by the tri-roller based on the position of the tri-roller.

NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A surgical impact tool comprising:
   a motor;

a roller assembly operatively connected to the motor and comprising a plurality of rollers, each of the plurality of rollers supported by a respective one of a plurality of roller arms;

an impact structure defining a spring and an impact cavity including forward and reverse impact surfaces disposed on opposite ends of the impact cavity, the impact structure comprising a wall comprising a plurality of thread elements connected to the wall and engageable with the roller assembly, each of the thread elements including a pair of helical end surfaces and a pair of axially extending surfaces that are engaged by the plurality of rollers;

a tool holder comprising an impact flange disposed within the impact cavity in between the forward and reverse impact surfaces; and wherein, during use:

rotation of the roller assembly against the helical end surfaces of the thread elements causes axial movement of the impact structure to apply a load on the spring, and engagement of the roller assembly against the pair of axially extending surfaces of the thread elements allows the spring to be unloaded and cause the impact structure to engage the impact flange.

2. The surgical impact tool of claim 1, wherein in a forward impact mode the impact flange of the tool holder is movable toward a rear end of the impact cavity when a tool implement is pressed against a workpiece and in a rearward impact mode the impact flange of the tool holder is movable toward a forward end of the impact cavity when the impact tool is pulled away from the workpiece.

3. The surgical impact tool of claim 2, wherein the forward impact mode includes rotating the roller assembly in a first direction against first helical ends of the thread elements and the rearward impact mode includes rotating the roller assembly in a second direction opposite the first direction and against second helical ends of the thread elements.

4. The surgical impact tool of claim 1, wherein the spring is formed integral with the wall.

5. The surgical impact tool of claim 1, wherein the spring includes at least three coil springs.

6. The surgical impact tool of claim 1, wherein the thread elements are connected to the wall by screws.

7. The surgical impact tool of claim 1, further comprising a gearbox connected to the motor.

8. The surgical impact tool of claim 7, wherein the gearbox and the motor are disposed within the spring of the impact structure.

9. The surgical impact tool of claim 1, further comprising:
a housing supporting the impact structure and the tool holder, the housing comprising a handle and a base;
a trigger disposed in the handle; and
a battery connected to the base.

10. The surgical impact tool of claim 9, further comprising:
a microphone disposed in the housing; and
a controller operative to control operation of the impact tool by voice command.

11. A surgical impact tool comprising:
a motor;
a roller assembly operatively connected to the motor and comprising:
a first roller supported by a first roller arm,
a second roller supported by a second roller arm, and
a third roller supported by a third roller arm;
an impact structure defining a spring and comprising forward and reverse impact surfaces, the impact structure defining an impact cavity with the forward and reverse impact surfaces disposed on opposite ends of the impact cavity, the impact structure comprising a wall comprising first, second, and third thread elements connected to the wall and engageable with the roller assembly, each of the first, second, and third thread elements including a pair of helical end surfaces and a pair of axially extending surfaces that are engaged by the first, second, and third rollers, respectively;
a tool holder comprising an impact flange disposed within the impact cavity in between the forward and reverse impact surfaces; and
wherein, during use:
rotation of the roller assembly against the helical end surfaces of the thread elements causes axial movement of the impact structure to apply a load on the spring, and
engagement of the roller assembly against the pair axially extending surfaces of the thread elements allows the spring to be unloaded and cause the impact structure to engage the impact flange.

12. The surgical impact tool of claim 11, wherein in a forward impact mode the impact flange of the tool holder is movable toward a rear end of the impact cavity when a tool implement is pressed against a workpiece and in a rearward impact mode the impact flange of the tool holder is movable toward a forward end of the impact cavity when the impact tool is pulled away from the workpiece.

13. The surgical impact tool of claim 12, wherein the forward impact mode includes rotating the roller assembly in a first direction against first helical ends of the thread elements and the rearward impact mode includes rotating the roller assembly in a second direction opposite the first direction and against second helical ends of the thread elements.

14. The surgical impact tool of claim 11, wherein the spring is formed integral with the wall.

15. The surgical impact tool of claim 11, wherein the spring includes at least three coil springs.

16. The surgical impact tool of claim 11, wherein the thread elements are connected to the wall by screws.

17. The surgical impact tool of claim 11, further comprising a gearbox connected to the motor.

18. The surgical impact tool of claim 17, wherein the gearbox and the motor are disposed within the spring of the impact structure.

19. The surgical impact tool of claim 11, further comprising:
a housing supporting the impact structure and the tool holder, the housing comprising a handle and a base;
a trigger disposed in the handle; and
a battery connected to the base.

20. The surgical impact tool of claim 19, further comprising:
a microphone disposed in the housing; and
a controller operative to control operation of the impact tool by voice command.

* * * * *